(12) United States Patent
Zvejniece et al.

(10) Patent No.: US 10,105,348 B2
(45) Date of Patent: Oct. 23, 2018

(54) USE OF 2-(5S-METHYL-2-OXO-4R-PHENYL-PYRROLIDIN-1-YL)-ACETAMIDE IN THE TREATMENT OF SEIZURES

(71) Applicant: Latvian Institute of Organic Synthesis, Riga (LV)

(72) Inventors: Liga Zvejniece, Marupe (LV); Maija Dambrova, Riga (LV); Baiba Svalbe, Sigulda (LV); Edijs Vavers, Incukalns (LV); Ivars Kalvins, Ikskile (LV); Grigorijs Veinbergs, Riga (LV); Ilmars Stonans, Riga (LV); Ilga Misane, Riga (LV); Maksims Vorona, Riga (LV); Aleksandrs Cernobrovijs, Riga (LV)

(73) Assignee: Latvian Institute of Organic Synthesis, Riga (LV)

( * ) Notice: Subject to any disclaimer, the term of this patent is extended or adjusted under 35 U.S.C. 154(b) by 0 days.

(21) Appl. No.: 15/743,522

(22) PCT Filed: Aug. 2, 2016

(86) PCT No.: PCT/IB2016/054641
§ 371 (c)(1),
(2) Date: Jan. 10, 2018

(87) PCT Pub. No.: WO2017/021881
PCT Pub. Date: Feb. 9, 2017

(65) Prior Publication Data
US 2018/0200227 A1    Jul. 19, 2018

(30) Foreign Application Priority Data
Aug. 3, 2015 (EP) .................. 15179448

(51) Int. Cl.
*A61K 31/401* (2006.01)
*A61P 25/08* (2006.01)
*A61K 31/4015* (2006.01)

(52) U.S. Cl.
CPC .......... *A61K 31/4015* (2013.01); *A61P 25/08* (2018.01)

(58) Field of Classification Search
CPC .......................... A61K 31/4015; A61P 25/08
See application file for complete search history.

(56) References Cited

FOREIGN PATENT DOCUMENTS

| EP | 1731149 | 12/2006 |
|---|---|---|
| EP | 2496555 | 8/2013 |
| WO | 2007/104780 | 9/2007 |

OTHER PUBLICATIONS

Guo et al., "Allosteric modulation of sigma-1 receptors elicits anti-seizure activities," British Journal of Pharmacology (2015) 172 4052-4065 (first published May 18, 2015). (Year: 2015).*
Zvejniece et al., "The cognition-enhancing activity of E1R, a novel positive allosteric modulator of sigma-1 receptors," British Journal of Pharmacology (2014) 171 761-771 (first published Nov. 6, 2013). (Year: 2013).*
International Search Report of ISA/EP for PCT/IB2016/054641 (dated Oct. 18, 2016).
Glozman O.M. et al., The synthesis and antispasmodic activity of 4-phenylpyrrolidone-2-acetamides, Pharmaceutical Chemistry Journal 14(11):776-780 (Nov. 1, 1980).
Savenkov A A e al., "nootropics and antioxidants in the complex therapy of symptomatic posttraumatic epilepsy," Database Medline [online] US National Library of Medicine (2013).

* cited by examiner

*Primary Examiner* — Theodore R. West
(74) *Attorney, Agent, or Firm* — Fish & Richardson P.C.

(57) ABSTRACT

Use of 2-(5S-Methyl-2-oxo-4R-phenyl-pyrrolidin-1-yl)-acetamide or its pharmaceutically acceptable salt in manufacture of a medicament for prophylaxis and treatment of seizure.

5 Claims, No Drawings

USE OF 2-(5S-METHYL-2-OXO-4R-PHENYL-PYRROLIDIN-1-YL)-ACETAMIDE IN THE TREATMENT OF SEIZURES

CROSS REFERENCE TO RELATED APPLICATIONS

This application is a national phase filing under 35 U.S.C. § 371 of International application number PCT/IB2016/054641, filed Aug. 2, 2016, which claims priority from EP application number 15179448.4 filed Aug. 3, 2015. The International Application published in English on Feb. 9, 2017 as WO 2017/021881 under PCT Article 21(2). The entire contents of the prior applications are incorporated herein by reference in their entirety.

TECHNICAL FIELD

The present invention relates to use of 2-(5S-Methyl-2-oxo-4R-phenyl-pyrrolidin-1-yl)-acetamide or its pharmaceutically acceptable salts in the treatment and prophylaxis of seizures.

BACKGROUND ART

Epilepsies are chronic neurological disorders in which clusters of nerve cells, or neurons, in the brain sometimes signal abnormally and cause seizures. Epilepsy can be considered as a spectrum disorder because of its different causes, different seizure types, its ability to vary in severity and impact from person to person, and its range of co-existing conditions. About 2.3 million adults and more than 450,000 children and adolescents in the United States currently live with epilepsy. Each year, an estimated 150,000 people are diagnosed with epilepsy. Epilepsy affects both males and females of all races, ethnic backgrounds, and ages. In the United States alone, the annual costs associated with the epilepsies are estimated to be $15.5 billion in direct medical expenses and lost or reduced earnings and productivity (http://www.ninds.nih.gov/disorders/epilepsy/detail_epilepsy.htm#1927231 09. Accessed Sep. 7 2015).

Despite the rapid expansion in the number and type of anticonvulsant drugs over the past two decades, the development of new anticonvulsants for refractory epilepsy is hampered by a lack of knowledge of physiological events that induce different seizure types. Furthermore, ~20-30% of patients are reported to suffer from refractory epilepsy, despite trying several medications, and an estimated 0.7-1.1 million patients with epilepsy across the seven major pharmaceutical markets (US, France, Germany, Italy, Spain, UK and Japan) are currently inadequately treated (Charlotte Mackey (2010). The anticonvulsants market. *Nat Rev Drug Discov* 9:265-266.).

Process of synthesis of 4R,5S-enantiomer of 2-(5S-Methyl-2-oxo-4R-phenyl-pyrrolidin-1-yl)-acetamide and its nootropic and cognition function enhancing properties has been described in EP2496555 (B1) (GRINDEKS JSC; 28 Aug. 2013).

SUMMARY OF INVENTION

Technical Problem

Epilepsy as a medical problem has significant socio-economical impact and there is a demand for new medicine for treatment of epileptic seizures.

Solution to Problem

It was surprisingly discovered that the 2-(5S-Methyl-2-oxo-4R-phenyl-pyrrolidin-1-yl)-acetamide significantly reduces clonic and tonic seizures.

DESCRIPTION OF EMBODIMENTS 2-(5S-Methyl-2-oxo-4R-phenyl-pyrrolidin-1-yl)-acetamide can be used in pharmaceutical preparations containing the compound, or a pharmaceutically acceptable salt thereof, in combination with a pharmaceutically acceptable carrier or diluents. Suitable pharmaceutically acceptable carriers include inert solid fillers or diluents and sterile aqueous or organic solutions. Thus, for oral administration the compounds can be combined with a suitable solid or liquid carrier or diluents to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. The injectable solutions can then be administered intravenously, intraperitoneally, subcutaneously, or intramuscularly.

Pharmaceutical composition for the prophylaxis or treatment of epileptic, tonic and/or clonic seizures comprising a pharmaceutically effective amount of 2-(5S-Methyl-2-oxo-4R-phenyl-pyrrolidin-1-yl)-acetamide or a pharmaceutically acceptable salt thereof and a pharmaceutically acceptable carrier, additive, diluent, cryoprotective or lyoprotective agent.

Pharmaceutical composition for the oral, parenteral, intravenous, intramuscular, epidural, intrathecal, inhalative or topical administration.

A method for the prophylaxis or treatment of epileptic, tonic and/or clonic seizures, wherein a pharmaceutically effective amount of the compound 2-(5S-Methyl-2-oxo-4R-phenyl-pyrrolidin-1-yl)-acetamide or a pharmaceutical composition is administered to an individual.

The composition of the present invention can be liquid preparation, preferably injection, vials or prefilled syringes, which can be prepared by conventional method. The injection, vials or prefilled syringes are prepared by lyophilizing 2-(5S-Methyl-2-oxo-4R-phenyl-pyrrolidin-1-yl)-acetamide or salt and then adding suitable excipients.

EXAMPLE

Animals and Treatment

Male ICR mice (Harlan Laboratories BV, Netherlands, ICR (CD-1)) weighing 23-25 g were housed under standard conditions (21-23° C., 50%±10% relative humidity, 12 h light-dark cycle) with unlimited access to standard food (R70 diet, Lactamin AB, Sweden) and water. All experimental procedures were carried out in accordance with guidelines of the EU Directive 2010/63/EU and were approved by the Ethics Council of Animal Protection at the Veterinary and Food Service, Riga, Latvia.

Chemoconvulsant-Induced Seizures

To accurately detect even slight modulatory effects on convulsive tendencies, we employed the more sensitive intravenous (i.v.) administration route of pentylenetetrazol (PTZ) administration (Loscher W, Honack D, Fassbender C P, Nolting B (1991). The role of technical, biological and pharmacological factors in the laboratory evaluation of anticonvulsant drugs. III. Pentylenetetrazole seizure models.

*Epilepsy Res* 8:171-189; Mandhane S N, Aavula K, Rajamannar T (2007). Timed pentylenetetrazol infusion test: a comparative analysis with s.c.PTZ and MES models of anticonvulsant screening in mice. *Seizure* 16:636-644) and used bicucculine (BIC) to inhibit the GABA pathway and to induce seizures (Meldrum B S (1975). Epilepsy and gamma-aminobutyric acid-mediated inhibition. *Int Rev Neurobiol* 17:1-36.). Chemoconvulsant-induced clonic and tonic seizures were initiated by inserting a 30-gauge needle into the tail vein of mice and infusing PTZ 1% or BIC 0.01% at a constant rate of 10 µl/1 s to restrained animals. Infusion was halted when forelimb clonus followed by tonic seizures of the full body were observed. Minimal doses of PTZ or BIC (mg/kg of mouse weight) necessary to induce clonic and tonic seizures were considered as an index of seizure threshold.

2-(5S-Methyl-2-oxo-4R-phenyl-pyrrolidin-1-yl)-acetamide (E1R) was administered i.p. at doses of 10 and 50 mg/kg. The test session was started 60 min after the administration of E1R or saline.

In the saline-treated mice, the doses of PTZ that induced clonic and tonic seizures in control mice were 24±2 and 45±3 mg/kg (Table 1) and doses of BIC were 0.38±0.02 and 0.75±0.09 mg/kg, respectively (Table 2). When E1R was administered at a dose of 50 mg/kg, the clonic and tonic seizures-inducing doses of PTZ and BIC were significant increased (Table 1; 2). As also seen in Table 1, E1R at a dose of 10 mg/kg significantly reduced the induction of tonic seizures by PTZ.

TABLE 1

Thresholds for PTZ-induced clonic and tonic seizures. E1R administered i.p. at doses of 10 and 50 mg/kg 60 min before 1% PTZ injection

| | Dose of PTZ, mg/kg ± SEM | |
|---|---|---|
| | Clonic seizure | Tonic seizure |
| Saline | 24 ± 1 | 45 ± 3 |
| E1R 10 mg/kg | 27 ± 2 | 64 ± 6* |
| E1R 50 mg/kg | 30 ± 1* | 80 ± 8* |

TABLE 2

Thresholds for BIC-induced clonic and tonic seizures. E1R administered i.p. at doses of 10 and 50 mg/kg 60 min before 0.01% BIC injection.

| | Dose of BIC, mg/kg ± SEM | |
|---|---|---|
| | Clonic seizure | Tonic seizure |
| Saline | 0.38 ± 0.02 | 0.75 ± 0.09 |
| E1R 10 mg/kg | 0.42 ± 0.02 | 0.88 ± 0.08 |
| E1R 50 mg/kg | 0.48 ± 0.03 | 1.15 ± 0.09* |

The invention claimed is:

1. A method for the prophylaxis or treatment of seizure, comprising administering to an individual in need thereof a pharmaceutically effective amount of 2-(5S-methyl-2-oxo-4R-phenyl-pyrrolidin-1-yl)-acetamide (I)

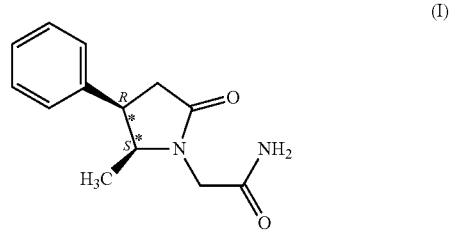

or a pharmaceutically acceptable salt thereof or a pharmaceutically effective amount of a pharmaceutical composition comprising 2-(5S-methyl-2-oxo-4R-phenyl-pyrrolidin-1-yl)-acetamide (I) or a pharmaceutically acceptable salt thereof and a pharmaceutically acceptable carrier, additive, diluent, cryoprotective or lyoprotective agent.

2. The method of claim 1, wherein the seizure is epileptic seizure.

3. The method of claim 1, wherein the seizure is tonic seizure.

4. The method of claim 1, wherein the seizure is clonic seizure.

5. The method of claim 1, wherein the administration is oral, parenteral, intravenous, intramuscular, epidural, intrathecal, inhalative, or topical administration.

* * * * *